United States Patent [19]
Prévost et al.

[11] Patent Number: 5,564,148
[45] Date of Patent: Oct. 15, 1996

[54] DENTAL PROSTHESIS CLEANING INSTRUMENT

[76] Inventors: Solange Prévost, 670 des Patriotes, Ste-Rose, Laval, Quebec, Canada, H7L 2M6; Geffrey Frenette, 1191 Boul. l'Ange Gardien North, L'Assomption, Quebec, Canada, J0K 1G0

[21] Appl. No.: 526,697

[22] Filed: Sep. 11, 1995

[51] Int. Cl.⁶ .............. A46B 9/04; A61C 17/00
[52] U.S. Cl. .............. 15/111; 15/105; 15/114; 15/167.1; 15/210.1; 15/229.11; 15/236.01; 15/DIG. 5; 132/309
[58] Field of Search .............. 15/105, 110, 111, 15/114, 167.1, 210.1, 229.11, 236.01, DIG. 5; 132/308, 309

[56] References Cited

U.S. PATENT DOCUMENTS

| | | | |
|---|---|---|---|
| D. 162,941 | 4/1951 | Ehrman | 15/111 |
| 1,475,789 | 11/1923 | Buckley | 132/309 |
| 1,487,075 | 3/1924 | Olson et al. | 132/309 |
| 1,540,911 | 6/1925 | Soneshein | 132/309 |
| 1,658,706 | 2/1928 | Carrott | 15/111 |
| 1,784,986 | 12/1930 | Eisenberg | 132/309 |
| 1,796,367 | 3/1931 | Grove | 132/309 |
| 1,937,857 | 12/1933 | Swope et al. | 15/167.1 |
| 2,028,519 | 1/1936 | Peterkin et al. | |
| 2,083,217 | 6/1937 | Brothers et al. | 15/111 |
| 2,464,321 | 3/1949 | Konczal | 15/167.1 |
| 4,449,934 | 5/1984 | Salam | 132/309 |
| 4,486,109 | 12/1984 | Rosofsky. | |

FOREIGN PATENT DOCUMENTS

| | | | |
|---|---|---|---|
| 121867 | 7/1946 | Australia | 15/111 |
| 207272 | 2/1940 | Switzerland | 15/111 |
| 240586 | 10/1925 | United Kingdom | 15/111 |
| 265690 | 2/1927 | United Kingdom | 15/167.1 |
| 711017 | 6/1954 | United Kingdom | 15/105 |
| 2178304 | 2/1987 | United Kingdom | 15/167.1 |

*Primary Examiner*—Mark Spisich
*Attorney, Agent, or Firm*—Swabey Ogilvy Renault; Guy J. Houle

[57] ABSTRACT

A dental prosthesis cleaning instrument is defined by an elongated member having a brush portion and a handle portion. The brush portion has a head formation formed at one end of the handle and a plurality of bristles extend from a surface portion thereof. The bristles terminate in an angled brushing surface defining an apex brush ridge adapted to clean angled surfaces of a dental prosthesis. A small scraping tool is provided at an opposed end of the handle portion. The scraping tool is dimensioned to scrape cavitated areas of the dental prosthesis. The scraping tool is a small spatula-shaped tool having a rounded end portion.

7 Claims, 3 Drawing Sheets

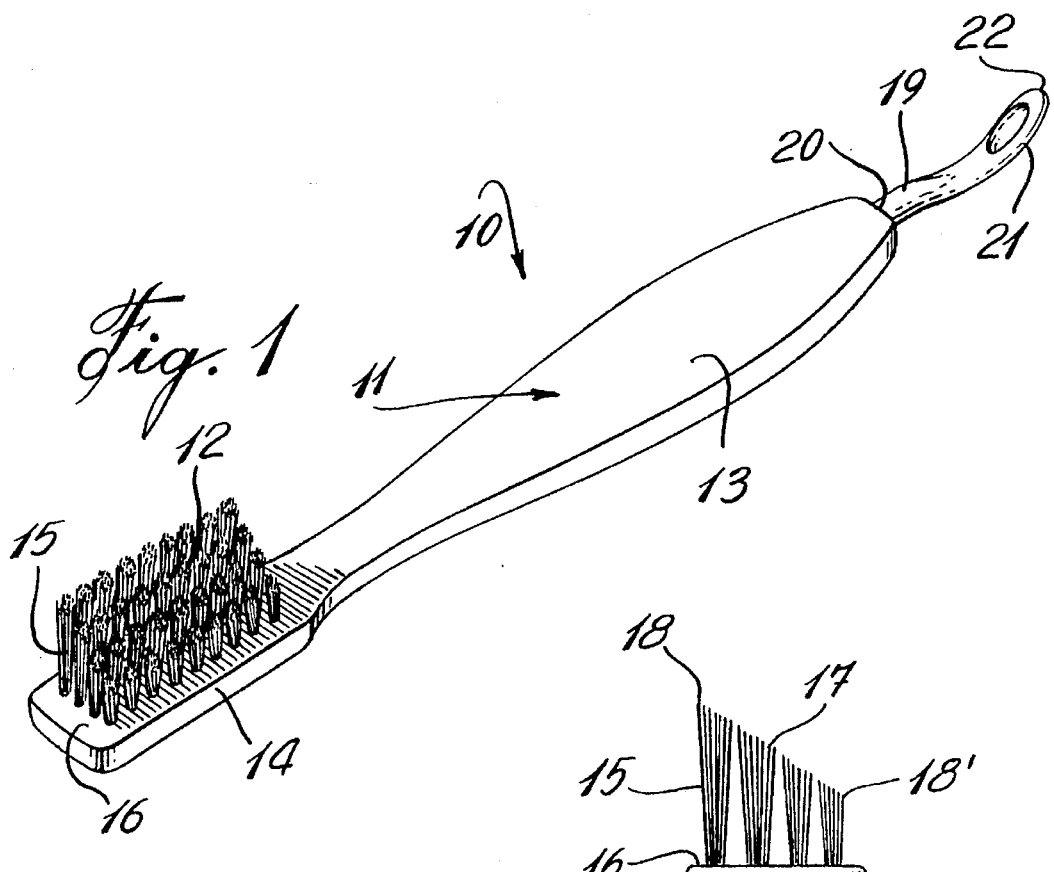
Fig. 1
Fig. 3
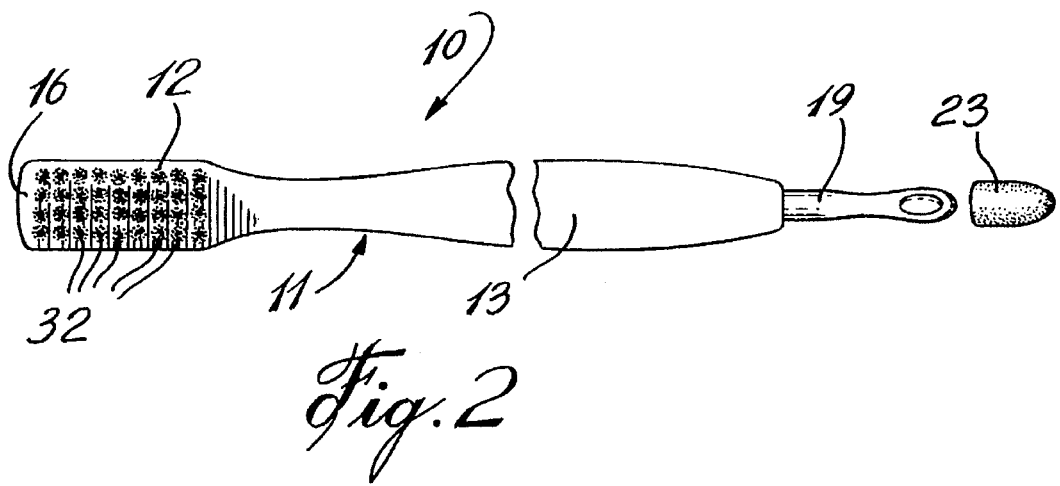
Fig. 2

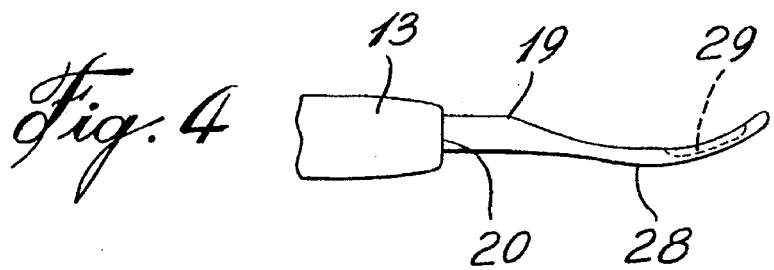
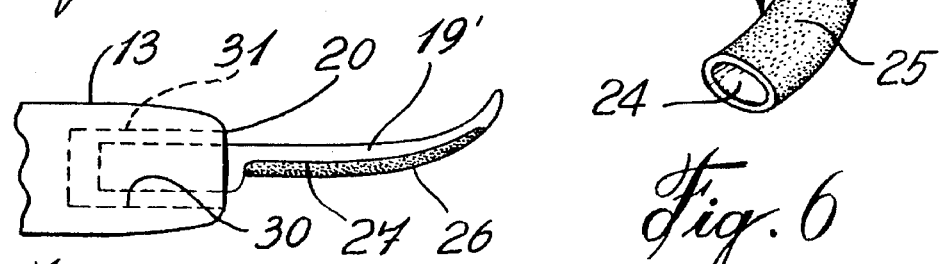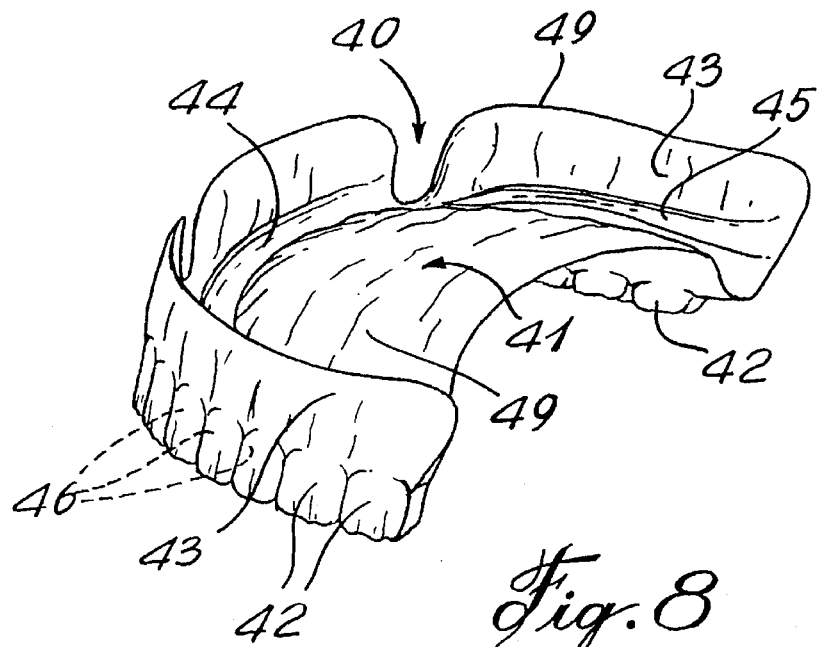

an angled brushing surface and a scraping tool at an opposed end of a handle and adapted to scrape cavitated areas which are hard to reach in a dental prosthesis.

DENTAL PROSTHESIS CLEANING INSTRUMENT

TECHNICAL FIELD

The present invention relates to a dental prosthesis cleaning instrument having a brush end portion with an angled brushing surface and a scraping tool at an opposed end of a handle and adapted to scrape cavitated areas which are hard to reach in a dental prosthesis.

BACKGROUND ART

Various shapes of toothbrushes are known for cleaning normal teeth and these comprise a brushing head on which soft bristles are disposed whereby not to damage the sensitive gums of a user person. The brush may have a variety of bristle stiffness but as a whole these are generally considered soft bristles. It is also known, as for example disclosed in U.S. Pat. Nos. 2,028,519 and 2,083,217 to provide a dental brush with an instrument provided at the opposed end of the brush head, such as a spoon whereby medicated products can be dispensed as such products are usually found in bathroom pharmacy cabinets. However, such spoon is of a size similar to that which we normally find in household utensils but is more convenient to the user when provided at the end of a toothbrush. The toothbrush may also be provided with a removable covering to massage the gums as shown in U.S. Pat. No. 4,486,109.

Most prior art toothbrushes are used for the cleaning of normal teeth and have been found unsatisfactory for the proper cleaning of dental prosthesis.

A dental prosthesis is formed of hard plastic materials which is set on a mold which carries the imprint of the wearer's upper pallet and upper and lower gums. This imprint contains distorted cavities which are useful for the retention of the dental prosthesis in the wearer's mouth. Without such cavities the dental prosthesis would be loose and would not be retained by the gums and upper pallet. It is known to provide a prosthesis brush which is comprised of a handle portion and a brush head formed of stiff bristles, much like the conventional toothbrush, but the head being relatively larger. This known dental prosthesis brush has a head similar to the conventional brush but formed of stiffer bristles and defining a flat brushing surface. However, hard-to-reach cavitated areas of the dental prosthesis are not cleaned by such brush.

It is essential for good hygiene to be able to clean these hard-to-reach areas on the inner surface of the dental prosthesis and also on the exterior surfaces in the cavities between the synthetic teeth as it is in those areas that plaque develops and hardens. The hardened plaque also forms surfaces which can be irritant to the wearer and may also affect the retention capacity of the dental prosthesis. Another disadvantage of the formation of plaque is that it carries bacteria and this bacteria generates unpleasant mouth odors.

SUMMARY OF INVENTION

It is therefore a feature of the present invention to provide a dental prosthesis cleaning instrument which is capable of effectively cleaning a dental prosthesis in hard-to-reach areas thereof and which substantially overcomes the above-mentioned disadvantages of the prior art.

Another feature of the present invention is to provide a dental prosthesis cleaning instrument having a brush end portion and a scraping tool provided at an opposed of a handle portion end whereby to clean hard-to-reach areas of a dental prosthesis.

Another feature of the present invention is to provide a dental prosthesis having a brush end and a spatula-shaped scraping tool at an opposed end and on which an abrasive cover may be removably secured and discarded after use.

Another feature of the present invention is to provide a dental prosthesis cleaning instrument wherein a file member may be secured to a surface area of the handle portion whereby to file away excessive plastics material on surface portions of a dental prosthesis.

According to the above features, from a broad aspect, the present invention provides a dental prosthesis cleaning instrument which is comprised of an elongated member having a brush portion and a handle portion. The brush portion has a head formation formed at one end of the handle and has a plurality of bristles extending from a surface portion thereof. The bristles terminate in an angled brushing surface defining an apex brush ridge adapted to clean hard-to-reach surfaces of a dental prosthesis. A small scraping tool is provided at an opposed end of the handle portion. The scraping tool is dimensioned to scrape cavitated areas of the dental prosthesis usually not accessible by the brush. 5 According to a further broad aspect of the present invention the scraping tool is a spatula-shaped tool having a rounded end portion.

According to a still further broad aspect of the present invention an abrasive cover is removably securable over the spatula-shaped tool.

BRIEF DESCRIPTION OF DRAWINGS

A preferred embodiment of the present invention will now be described with reference to the accompanying drawings in which:

FIG. 1 is a perspective view of the dental prosthesis cleaning instrument of the present invention;

FIG. 2 is a plan view of the cleaning instrument of FIG. 1 and showing an abrasive cover which is removably securable over the spatula-shaped tool;

FIG. 3 is an end view of the brush end of the cleaning instrument;

FIG. 4 is a fragmented side end view of the cleaning instrument showing the shape of the scraping tool;

FIG. 5 is a view similar to FIG. 4 but showing the scraping tool integrally formed with the handle portion;

FIG. 6 is a perspective view showing the construction of the abrasive cover;

FIG. 7 is a side end view of the cleaning instrument handle showing another embodiment wherein the scraping tool may have different shapes and may be removably securable in the free end portion of the brush handle;

FIG. 8 is a perspective view of a dental prosthesis illustrating cavitated areas thereof;

DESCRIPTION OF PREFERRED EMBODIMENTS

Figure 9:
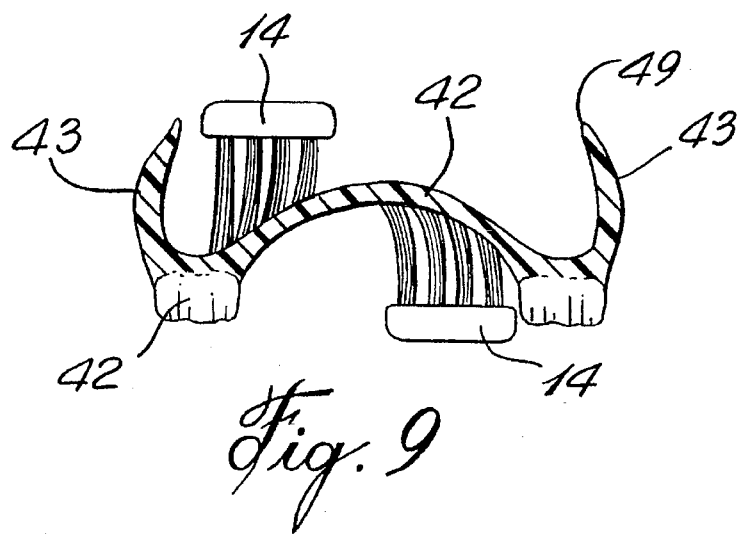
FIG. 9 is a section view of a dental prosthesis showing curved surfaces thereof and the use of the brush head of the cleaning instrument of the present invention.

Referring now to the drawings and more particularly to FIGS. 1 to 3, there is shown generally at 10 the dental prosthesis cleaning instrument of the present invention. The instrument is comprised of an elongated member 11 having a brush end portion 12 and a handle portion 13. The brush portion 12 has a head formation 14 formed at one end of the handle portion 13 and has a plurality of stiff bristles 15 extending from a flat top surface 16 of the head formation 14.

As shown in FIG. 3, the bristles 15 terminate in an angled brushing surface 17 defining an apex brush ridge 18 which is adapted to clean angled surfaces and hard-to-reach areas, as will be described later, of a dental prosthesis.

As shown in FIGS. 1 and 2, a small scraping tool 19 is provided at an opposed end 20 of the handle portion 13 and is dimensioned to scrape cavitated areas, as will be described later, of a dental prosthesis. The scraping tool as hereinshown is a spatula-shaped tool having a spatula end 21 which has a rounded free end 22. An abrasive cover 23 may be removably secured over the spatula-shaped tool 19.

As shown in FIG. 6, the abrasive cover 23 is formed as a pouch of stretchable material having an open end 24 which fits over the rounded end 22 of the spatula-shaped end 21. An abrasive surface 25 is provided about the pouch and this may be a soft abrasive whereby to remove plaque from hard-to-reach areas of a dental prosthesis. A cleaning paste or similar substance (not shown) may also be placed over the pouch to help in the removal of plaque and the sanitation of the dental prosthesis, particularly in hard-to-reach cavitated areas thereof. A polish material may also be applied to polish the teeth, including the natural teeth of the user. This pouch is usually discarded after use as it will contain bacteria which is present in the plaque or foodstuff. The pouch may also be provided with abrasives of different grades depending on the intended use and it could also be used to file away plastic material from the prosthesis in areas which may be irritable to the user. However, for this latter use there could also be provided an abrasive file surface 26, as shown in FIG. 7, on the back face 27 of the scraping tool 19.

Referring now to FIGS. 4, 5 and 7, there will be described various embodiments of the construction of the scraping tool 19. As shown in FIG. 4, which is a side view of the end portion of the handle portion 13 on which the scraping tool 19 is secured, the tool may have an arcuate shape portion 28 with a shallow depression 29 in an end area forming a spoon on which plaque or other materials, such as foodstuff, which is lodged within cavitated areas of a dental prosthesis, accumulate during a scraping operation. The scraping tool as hereinshown is formed as a metal insert which is injection molded in the end 20 of the brush 10.

As shown in FIG. 5, the scraping tool 19 may be integrally molded with the handle portion 13 and formed of rigid plastic material. The tool may also have a sharp end portion 30 to provide better scraping. However, it is preferable that this tool be formed of metal as it does not wear as easily as plastic.

As shown in FIG. 7, a connecting insert 19' may be molded inside the end portion 31 of the handle portion 13 of the brush whereby to removably connect therein scraping tools 19' of different shapes whereby to reach various types of difficult cavitated areas of dental prosthesis.

Referring to FIG. 2 which illustrates a preferred embodiment of the present invention, it can be seen that the brush portion 12 is formed as a generally rectangular brushing surface having a straight flat angled surface 17 as shown in FIG. 3, and with an apex brush ridge 18 located at an elongated side edge of the surface and sloping in a generally flat plane to a short bristled opposed side edge 18'. The bristles are formed of stiff filamentary fibers disposed in groups 32. As shown in FIG. 2 there are four rows of seven groups of bristles extending from the flat top surface portion 16.

Referring now to FIG. 8 there is illustrated the construction of a dental prosthesis 40 which is comprised essentially of a plastic molded mouthpiece 41 having a plurality of teeth shaped formations 42 molded therein. The mouthpiece 41 has a pallet portion 39 which has a curvature, as shown in FIG. 9, to fit the pallet of the user's mouth. It also has a gum surrounding portion 43 which has a variety of shapes to fit about the gums of the user. Depending on the shape of the gum of a user, this portion 43 may have deep cavities or hardly any cavities, and in this latter case it becomes difficult to secure dental prosthesis to a person's mouth. However, these cavities provide good retention to the gums in the mouth of the wearer. Such deep cavities are usually located in the frontal side areas 44 of the mouth, as shown in FIG. 8, or in the side areas 45 of the prosthesis. Although FIG. 8 shows a full denture prosthesis, it is also known that partial dentures may be provided and these usually also have hard-to-reach cavitated areas to receive the gums or portions thereof.

Figure 10:
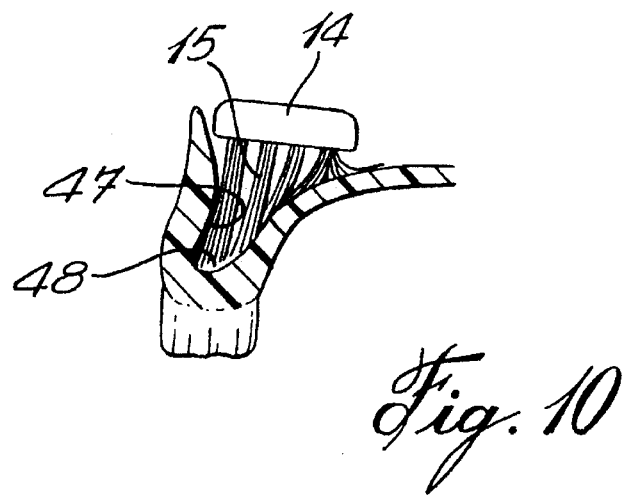
FIGS. 10 and 11 are section views of a dental prosthesis showing hard-to-reach cavitated areas thereof.
Figure 11:
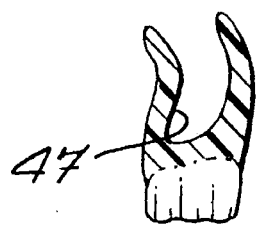

As shown in FIG. 9, because the angled brush portion 12 is angled, it is easy to clean the opposed surfaces of the pallet portion 39, which is arcuate, and depending on the shape of the prosthesis the brush may be suitable to clean the entire prosthesis. However, there are also hard-to-reach areas of a prosthesis between the teeth which define cavities as shown at 46 in FIG. 8, and these areas can develop plaque and the brush head is not sufficient to remove this plaque. As shown in FIGS. 10 and 11, hard-to-reach cavities are designated by reference numerals 47 and these are usually lodged on the backside of the gum cavities 48. The angled bristles 15 (see FIG. 10) are not suitable to reach these areas and this is where foodstuff accumulates and plaque forms to eventually reshape the gum cavities 48 causing irritation to the wearer and also resulting in bad mouth odors due to the bacteria which is retained in the plaque. The shape of the scraping instrument makes it possible to remove plaque in these areas. Chemical products may also be used to soften the plaque to permit easy removal thereof by the spatula-shaped tool 19 which may have a variety of shapes to reach these areas. The abrasive cover or the file 26 may also be used to reshape the irritable edges 49 of the dental prosthesis, as shown in FIGS. 8 and 9.

It is within the ambit of the present invention to cover any obvious modifications of the preferred embodiment described herein, provided such modifications fall within the scope of the appended claims.

We claim:

1. A dental prosthesis cleaning instrument, said instrument comprising an elongated member having a brush portion and a handle portion, said brush portion having a head formation formed at one end of said handle portion and having a plurality of bristles extending from a surface portion thereof, said bristles terminating in an angled brushing surface defining an apex brush ridge adapted to clean angled surfaces of a dental prosthesis and a small spatula-shaped scraping tool having a rounded free end and provided at an opposed end of said handle portion, said scraping tool being dimensioned to scrape cavitated areas of said dental prosthesis and a discardable abrasive pouch of stretchable material removably securable over said spatula-shaped tool.

2. A dental prosthesis cleaning instrument as claimed in claim 1 wherein said angled brushing surface is a generally rectangular surface having a straight flat angled surface with said apex brush ridge located at an elongated side edge of said surface portion and sloping in a generally flat plane to a short bristled opposed side edge.

3. A dental prosthesis cleaning instrument as claimed in claim 2 wherein said bristles are stiff filamentary bristles disposed in groups, there being four rows of seven groups of bristles extending from said surface portion, said surface portion being a flat surface area of said head formation.

4. A dental prosthesis cleaning instrument as claimed in claim 1 wherein said spatula-shaped tool is a metal spatula, said rounded free end portion defining a spoon formation.

5. A dental prosthesis cleaning instrument as claimed in claim 1 wherein said spatula-shaped scraping tool is removably secured to said opposed end of said handle portion for replacement with scraping tools of different shapes.

6. A dental prosthesis cleaning instrument as claimed in claim 1 wherein there is further provided an abrasive file member secured to a surface area of said scraping tool, said file member having an abrasive surface for filing plastic material of a mouthpiece of said dental prosthesis.

7. A dental prosthesis cleaning instrument as claimed in claim 1 wherein said spatula-shaped tool is integrally formed with said handle portion, said elongated member being molded of plastic material.

\* \* \* \* \*